(12) United States Patent
Martello

(10) Patent No.: US 10,864,518 B2
(45) Date of Patent: Dec. 15, 2020

(54) DEVICE FOR COLLECTING, TRANSFERRING, AND STORING SAMPLES OF A BIOLOGICAL AND/OR CHEMICAL MATERIAL

(71) Applicant: Copan Italia S.p.A., Brescia (IT)

(72) Inventor: Giorgio Martello, Brescia (IT)

(73) Assignee: Copan Italia S.p.A., Brescia (IT)

( * ) Notice: Subject to any disclaimer, the term of this patent is extended or adjusted under 35 U.S.C. 154(b) by 211 days.

(21) Appl. No.: 15/772,245

(22) PCT Filed: Oct. 21, 2016

(86) PCT No.: PCT/IB2016/056340
§ 371 (c)(1),
(2) Date: Apr. 30, 2018

(87) PCT Pub. No.: WO2017/077415
PCT Pub. Date: May 11, 2017

(65) Prior Publication Data
US 2018/0361375 A1    Dec. 20, 2018

(30) Foreign Application Priority Data

Nov. 3, 2015  (IT) .......................... 102015000068584

(51) Int. Cl.
| | |
|---|---|
| *A61F 13/38* | (2006.01) |
| *G01N 1/02* | (2006.01) |
| *B01L 3/00* | (2006.01) |
| *A61B 10/00* | (2006.01) |

(52) U.S. Cl.
CPC ........ *B01L 3/5029* (2013.01); *A61B 10/0045* (2013.01); *B01L 3/5023* (2013.01);
(Continued)

(58) Field of Classification Search
CPC .. A61B 10/0045; A61B 10/0051; G01N 1/02; G01N 2001/028
(Continued)

(56) References Cited

U.S. PATENT DOCUMENTS 5,169,789 A * 12/1992 Bernstein ........... G01N 33/5302
422/413
5,308,580 A *  5/1994 Clark ...................... B01L 3/502
422/419
(Continued)

FOREIGN PATENT DOCUMENTS

EP           1608268 B1    11/2007
WO     WO9003959 A1     4/1990
(Continued)

OTHER PUBLICATIONS

PCT International Search Report and Written Opinion of the International Searching Authority, PCT/IB2016/056340, dated Feb. 28, 2017, 14 pages.

*Primary Examiner* — Jill A Warden
*Assistant Examiner* — Brittany I Fisher
(74) *Attorney, Agent, or Firm* — Fish & Richardson P.C.

(57) ABSTRACT

A device for collecting, transferring, and storing samples of a biological and/or chemical material, wherein the device comprises: a support body, developing along a main longitudinal direction between a first end and a second end opposite to each other and connected by an intermediate portion elongate in the main longitudinal direction, a collection portion engaging the first end and configured to collect a quantity of a sample of a biological and/or chemical material, the collection portion being defined at least by a first coating layer realized on the first end and made from an elastically deformable material and by a second coating layer consisting of a layer of flocked fibers, the second coating layer being realized through a fiber flocking process (Continued)

on the first coating layer and being configured to absorb a quantity of liquid including at least one sample of a biological and/or chemical material.

17 Claims, 4 Drawing Sheets

(52) U.S. Cl.
CPC .............. *B01L 3/5055* (2013.01); *G01N 1/02* (2013.01); *A61B 10/0051* (2013.01); *B01L 2200/141* (2013.01); *B01L 2300/043* (2013.01); *B01L 2300/069* (2013.01); *B01L 2300/0809* (2013.01); *B01L 2300/123* (2013.01); *G01N 2001/028* (2013.01)

(58) Field of Classification Search
USPC .......................................................... 422/561
See application file for complete search history.

(56) References Cited

U.S. PATENT DOCUMENTS

| | | | | |
|---|---|---|---|---|
| 6,115,873 | A * | 9/2000 | Dunkley | A45D 40/26 15/209.1 |
| 7,993,283 | B1 * | 8/2011 | Altschul | G01N 21/78 600/573 |
| 2004/0161855 | A1 * | 8/2004 | Kvasnik | B01L 3/545 436/165 |
| 2004/0171173 | A1 * | 9/2004 | Eckermann | A61B 10/0045 436/514 |
| 2009/0208371 | A1 * | 8/2009 | Hannant | A61B 10/0045 422/400 |
| 2010/0106057 | A1 * | 4/2010 | Harvey | B01L 3/505 600/573 |
| 2011/0282243 | A1 | 11/2011 | Nakatani | |
| 2013/0344616 | A1 | 12/2013 | Triva | |
| 2014/0100480 | A1 * | 4/2014 | Pierce | A61B 10/0045 600/573 |
| 2015/0047441 | A1 * | 2/2015 | Zhang | G01N 33/5436 73/863.23 |

FOREIGN PATENT DOCUMENTS

| | | |
|---|---|---|
| WO | WO2004021855 A1 | 3/2004 |
| WO | WO2004086979 A1 | 10/2004 |
| WO | WO2008099196 A1 | 8/2008 |
| WO | WO2014001940 A1 | 1/2014 |
| WO | WO2014207598 A1 | 12/2014 |
| WO | WO2015052607 A1 | 4/2015 |

* cited by examiner

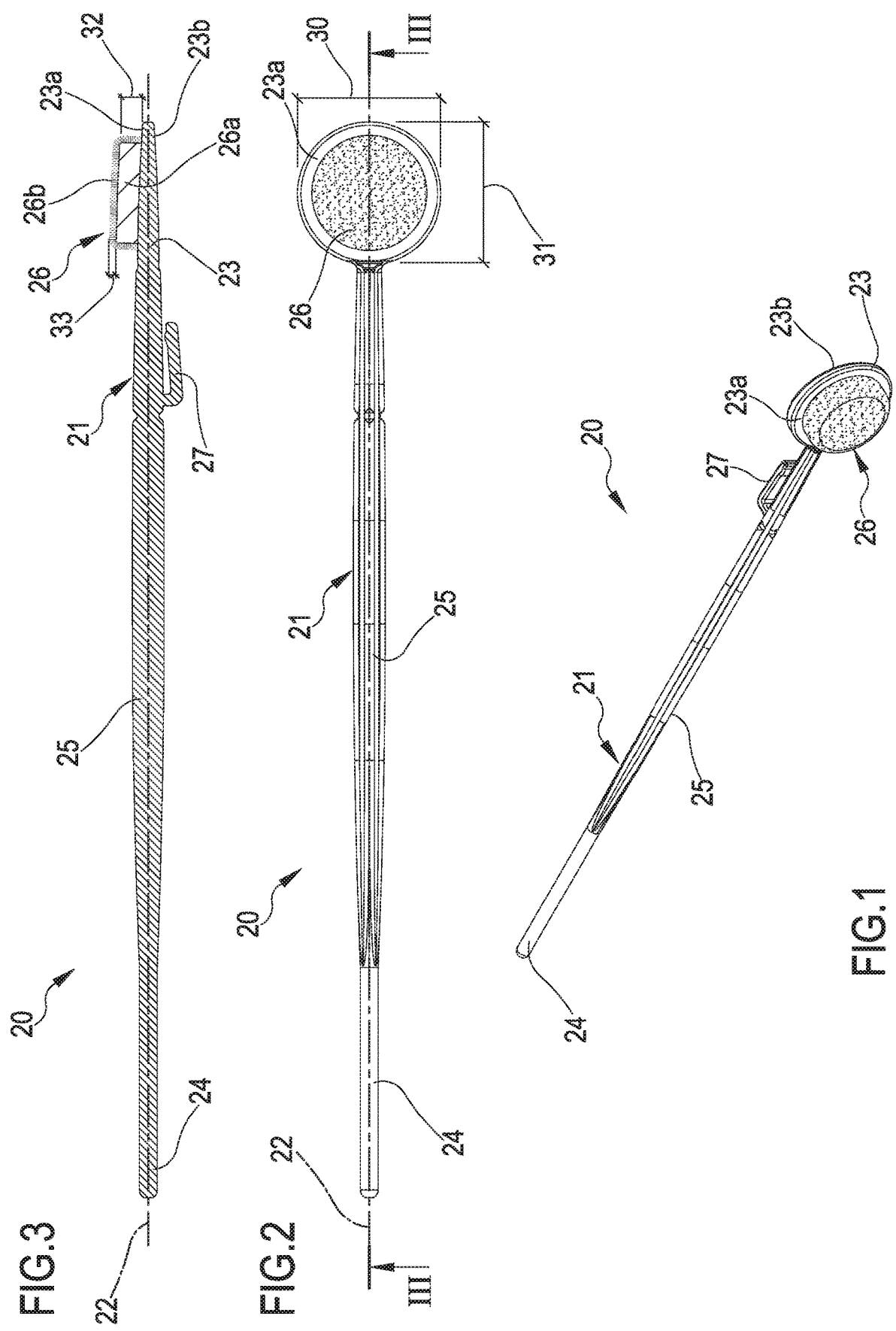

DEVICE FOR COLLECTING, TRANSFERRING, AND STORING SAMPLES OF A BIOLOGICAL AND/OR CHEMICAL MATERIAL

CROSS-REFERENCE TO RELATED APPLICATIONS

This application is a U.S. National Phase application under U.S.C. § 371 and claims the benefit of priority to International Application No. PCT/IB2016/056340, filed Oct. 21, 2016, which claims priority to Italian Patent Application No. IT102015000068584, filed Nov. 3, 2015, the contents of which are hereby incorporated by reference.

DESCRIPTION

The concepts herein refer to a device for collecting, transferring, and storing samples of a biological and chemical material. The concepts herein also concern a kit comprising such device and a method for collecting, transferring, and storing samples of a biological and/or chemical material by such device and such kit. The concepts herein also concern a method for implementing a device for collecting, transferring, and storing samples of a biological and/or chemical material. The concepts herein find, for instance, a particular application for collecting, transferring and/or storing buccal and/or lingual samples, but it can also be applied to numerous further sample collecting types. The use of various types of collection devices, which are provided at least with a collection portion suitable for collecting biological and/or chemical samples and a support body suitable for making it possible to handle the collection element itself is known. Collection devices are known having collection portions of different types, for instance made up of cotton fibers wound around a rod, semi-rigid fibers suitable for scratching a surface and performing a collection in an essentially "mechanical" manner, or an absorbing material of a spongy or foamy type mounted on the rod, etc. Devices are also known which are referred to "flocked swabs", comprising an elongate support body and a plurality of flocked fibers at one end of the support body to define a collection portion suitable for absorbing the mentioned analytes or biological samples. Such type of device is known from patent EP1608268B1 (Triva), deriving from WO2004/086979 A1. Further solutions related to such type of product are described in WO2014/207598 (Triva) and WO2015/052607 A1 (Triva). Technical solutions are also known, in particular in the case of buccal or lingual collections, whereby, after collecting a sample of a biological material, the sample itself is transferred onto a different medium suitable for making it possible to store the sample even for a long period of time. For instance, the practice is known of transferring the samples collected by way of the mentioned collection devices onto matrix media or chemically treated papers to make it possible for the samples of material to be absorbed and stored. Such type of papers is known, for instance, from patent application WO9003959 (Burgoyne). Technical solutions are also known which make it possible to collect a biological sample and to transfer it onto the mentioned storage papers by way of an appropriate kit, which comprises a collection device as well as a medium to house the storage paper. Such kits are illustrated, for instance, in patent application WO2008/099196 (Harvery) and in patent application WO2014/001940 (Triva) corresponding to US2013/344616 A1. Such solutions support the possibility of moving, in a controlled manner, the collection device from a sample transfer position, where it is in contact with the storage paper, to a rest and transfer position, wherein such elements are spaced away. However, a correct transfer of samples and a correct operation of such kits might be difficult in some situations. As a matter of fact, a correct transfer of a collected sample from the collection portion of the collection device to the storage paper, or to another medium, is affected by numerous factors, among which: the material and the arrangement of the collection portion of the collection device, the type of the paper, the material and the shape of the kit housing body accommodating the storage paper and the collection device, the degree of elasticity of the movable portion that the collection device is coupled with, the force that is applied by a user to make the collection portion and the storage paper get closer, and so on.

Consequently, in some cases a transfer might take place incorrectly, in a non-homogeneous manner, or to an insufficient extent, and this might entail even severe consequences in term of reliability of the analysis performed on a sample and a complete traceability thereof. The main object of the concepts herein is to solve one or more of the problems encountered in the known art. An object of the concepts herein is to provide a device and a method for collecting, transferring, and storing samples of a biological and/or chemical material that make it possible to guarantee a reliable and completely traceable storage of the collected sample.

Another object is to provide a device and a method that offer a high reliability in any conditions of use and as much independent as possible of the mode of use by a specific professional user. Another object is to provide a device and a method that allow for an optimum transfer of a collected sample from a collection device to a storage paper or to another storage or analysis medium. Another object is to provide a device and a method that are easy to use. It is also an object of the concepts herein to provide a device and a method that make it possible to minimize the risk of contamination for the collected samples. It is a further object of the concepts herein to provide a device and a method that are simple and economical to implement. These objects and others, which will be more apparent from the following description, are substantially achieved by a device and by a method for collecting, transferring, and storing samples of a biological and/or chemical material according to the contents of one or several of the attached claims, taken alone or in any combinations between them, or in any combinations with one or more of the further aspects described below. Further aspects of a device for collecting, transferring, and storing samples of a biological and/or chemical material, which can be taken in any combinations between them and/or with the attached claims, are expressed below. In a further aspect, combinable with any of the attached dependent claims of the device and/or with any of the further aspects indicated below, the concepts herein also concern a device for collecting, transferring, and storing samples of a biological and/or chemical material, wherein the device comprises a support body, developing along a main longitudinal direction between a first end and a second end, opposite to each other and connected by an intermediate portion featuring an elongate shape in the main longitudinal direction; a collection portion engaging the first end and configured to collect a quantity of a sample of a biological and/or chemical material, wherein the collection portion is defined at least by a first coating layer realized on the first end made from an elastically deformable material and wherein the first coating layer consists of a plurality of separate sub-portions and/or is provided with a plurality of pre-indented sub-portions and/or is provided with indentations realized so as to define a plurality of at least partially separate sub-portions, so as to facilitate the detachment of at least one individual sub-portion of the first coating layer, and of a corresponding sub-portion of the second layer, from the first end at a time following the sample collection time. In a further aspect, the collection device is a device for a buccal collecting of samples. In a further aspect, the collection device is a swab. In a further aspect, the collection device is a buccal and/or lingual swab. In a further aspect, the collection portion is configured to absorb a sample of a biological and/or chemical material. In a further aspect, the first coating layer is made from a synthetic sponge. In a further aspect the first coating layer is made from an expanded resin. In a further aspect, the first coating layer is made from one or more of the following materials: expanded polyethylene, EVA, LDPE, expanded polyurethane, polyether, polyester, Stratocell® (a laminated polyethylene foam, which can have a closed-cell structure and have low-density, medium density or high density), antistatic, FOAM, Plastazote® (a closed-cell cross-linked polyethylene foam), rubber mousse, latex, Dryfeel® (an opel cell reticulated polyether foam which can be treated with biocide against bacteria and fungi). In a further aspect, the first layer is made from a liquid-impermeable and/or hydrophobic material. In a further aspect, the first layer is liquid-impermeable. In a further aspect, the first layer is made liquid-impermeable by coating it with an adhesive material. In a further aspect, the first layer is made from an hydrophobic material of a "coarse grain" type and/or having "big-size cells". In a further aspect, the first layer is made from a sponge of a "coarse grain" type and/or having "big-size cells". In a further aspect, a first layer of an adhesive material is provided between the first coating layer and the first end to attach the first coating layer at least to the front face of the first end. In a further aspect, a second layer of an adhesive material is provided between the first coating layer and the second coating layer, to make it possible for the flocked fibers to adhere to the first coating layer. In a further aspect, the adhesive material is a vinylic adhesive. In a further aspect, the front face and the rear face are substantially equal to each other and/or symmetrical. In a further aspect, the thickness of the first end, as measured between the first face and the second face and/or in a direction perpendicular to the first face and/or to the second face, ranges from 0.5 mm to 5 mm, or from 0.7 to 4 mm, or from 1 to 2.5 mm. In a further aspect, the surface of the front face and/or of the rear face ranges from 20 mm$^2$ to 1250 mm$^2$, or from 80 mm$^2$ to 700 mm$^2$, or from 120 mm$^2$ to 400 mm$^2$. In a further aspect, the width of the front face and/or of the rear face, in a direction perpendicular to the main longitudinal direction, ranges from 5 mm to 40 mm, or from 10 mm to 30 mm, or from 12 mm to 22 mm. In a further aspect, the diameter of the front face and/or of the rear face ranges from 5 mm to 40 mm, or from 10 mm to 30 mm, or from 12 mm to 22 mm. In a further aspect, the length of the fibers of second coating layer thickness of the second coating layer is less than 3 mm, or less than 2 mm, or less than 1 mm. In a further aspect, the length of the fibers of the second coating layer thickness of the second coating layer is greater than 0.3 mm, or greater than 0.45 mm, or greater than 0.6 mm.

In a further aspect, the first coating layer completely covers the front face of the first end. In a further aspect, the first coating layer completely covers the rear face of the first end. In a further aspect, the first coating layer completely covers the first end. In a further aspect, the second coating layer completely covers the first coating layer. In a further aspect, the first coating layer covers at least 10%, or at least 30%, or at least 50%, or at least 70% of the front face of the first end. In a further aspect, the first coating layer covers 100%, or less than 90%, or less than 80%, or less than 70% of the front face of the first end. In a further aspect, the second coating layer covers at least 10%, or at least 30%, or at least 50%, or at least 70% of the front face of the first end. In a further aspect, the second coating layer covers 100%, or less than 90%, or less than 80%, or less than 70% of the front face of the first end. In a further aspect, the second coating layer covers at least 10%, or at least 30%, or at least 50%, or at least 70% of the first coating layer. In a further aspect, the second coating layer covers 100%, or less than 90%, or less than 80%, or less than 70% of the first coating layer. In a further aspect, the support body is provided, preferably in correspondence with the intermediate portion, with a coupling portion, suitable for making it possible the connection of the device to an engagement element of a kit for collecting, transferring, and storing samples of a biological and/or chemical material. In a further aspect, the coupling portion is realized on the same side as the rear face and on the opposite side with respect to the front face. In a further aspect, the collection portion is also realized and engaged to the rear face of the first end. In a further aspect, the first coating layer has a surface extension less than the surface extension of the front face of the first end. In a further aspect, the first coating layer has a surface extension less than the surface extension of the rear face of the first end. In a further aspect, the second coating layer has a surface extension less than the surface extension of the first coating layer. In a further aspect, the front face and/or the rear face have a perimetric development of the front face and/or of the rear face, that is curvilinear or substantially elliptical or substantially circular or polygonal and substantially triangular or substantially quadrangular. In a further aspect, the main longitudinal direction coincides with a straight line. In a further aspect, the main longitudinal direction is a curved line, and the support body has an at least partially curvilinear longitudinal development. In a further aspect, indentations cut in the first coating layer extend in correspondence with at least one part of the thickness of the first coating layer, in order not to completely separate the sub-portions before collecting a sample. In a further aspect, the indentations extend in correspondence with the full thickness of the first coating layer, to completely separate the sub-portions even before collecting a sample. In a further aspect, the indentations develop in a direction perpendicular to the surface of the first coating layer intended for receiving the second coating layer. In a further aspect, the first coating layer features, in correspondence with at least one sub-portion of the first coating layer, at least one attachment bulge integral with said sub-portion and suitable for making the attachment and the detachment of such sub-portion from the remaining collection portion, easier. In a further aspect, the attachment bulge consists of a tang extending from a lateral surface of the first coating layer perpendicular to the surface of the first coating layer on which the second coating layer is applied or is intended for being realized. In a further aspect, the support body has a length, in its longitudinal extension, ranging from 50 mm to 200 mm, or from 100 mm to 200 mm, or from 145 mm to 155 mm.

In a further aspect, the support body has, in correspondence with the collecting portion, a diameter in a cross-section perpendicular to its longitudinal extension ranging from 0.8 mm to 5 mm, or from 1 mm to 4 mm, or from 2 mm to 3 mm, or from 2.2 mm to 2.8 mm. In a further aspect, the support body features, in correspondence with the intermediate portion, a diameter in a cross-section perpendicular to its longitudinal extension, ranging from 1 mm to 10 mm, or from 2 mm to 8 mm, or from 3 mm to 6 mm, or from 4 mm to 5 mm. In a further aspect, the collection portion has a length ranging from 5 mm to 40 mm, or from 10 mm to 30 mm, or from 15 mm to 25 mm, or from 12 mm to 20 mm. In a further aspect, la collection portion has a width, in a direction perpendicular to the main longitudinal direction, or a diameter, ranging from 5 mm to 40 mm, or from 10 mm to 30 mm, or from 15 mm to 25 mm, or from 12 mm to 22 mm. In a further aspect, the collection portion is configured to collect or absorb a substantially known quantity of a sample. In a further aspect, the fibers are arranged on the first coating layer in a substantially orderly manner. In a further aspect, the fibers are arranged on the first coating layer so as to form a substantially continuous layer. In a further aspect, the fibers are arranged on the first coating layer so as to define a plurality of capillary interstices suitable for absorbing a sample by capillarity. In a further aspect, the fibers feature a count ranging from 1 to 10 dtex, or from 2 to 7 dtex, or from 3 to 5 dtex. In a further aspect, the fibers feature a length ranging from 0.2 mm to 3 mm, or from 0.4 mm to 2 mm, or from 0.6 mm to 1.5 mm. In a further aspect, the fibers are made from a polyamide (PA or nylon) and/or from rayon and/or from polyester and/or a carbon fiber and/or from an alginate and/or from a natural fiber and/or from cotton and/or from a mix of such materials. In a further aspect, the collection portion features a surface density of fibers on the first coating layer ranging from 50 to 1000 fiber per $mm^2$, or from 100 to 500 fibers per $mm^2$. In a further aspect, the support body is made from a substantially rigid or partially flexible material. In a further aspect, the support body is made from a plastic material. In a further aspect, the support body is made from a plastic polymer or from a co-polyester or from polystyrene or from nylon/polyamide. In a further aspect, the concepts herein also concern the use of a device in accordance with any of the above-mentioned claims and/or aspects, for collecting, transferring, and storing a sample of a biological and/or chemical material or for collecting, transferring, and storing a sample of a buccal and/or lingual biological material. Further aspects of a kit for collecting, transferring, and storing samples of a biological and/or chemical material, which might be collected in any combinations between them and/or with the attached claims, are expressed below. In a further aspect of its own, the engagement element is configured to selectively and removably engage the collection device to the housing body, in correspondence with the housing seat. In a further aspect, the engagement element is configured to selectively and removably engage the collection device to the operating portion. In a further aspect of its own, the collection device is provided with at least one coupling portion in correspondence with which it can be selectively and removably coupled with the engagement element. In a further aspect of its own, the engagement element is configured to removably engage the collection device to the operating portion. In a further aspect of its own, the storage element is a chemically treated paper suitable for storing samples of a biological material and/or is a paper comprising at least one substance suitable for storing a sample of a biological material. In a further aspect of its own, the engagement element is suitable for defining at least one first mounting position for the collection device in correspondence with which a contact and a transfer of a biological material take place from the collection portion of the collecting element to the storage portion. In a further aspect of its own, the engagement element is suitable for defining at least one second mounting position for the collecting element in correspondence with which the collection portion is spaced away from the storage portion and consequently there is no contact nor transfer of a biological material from the collection portion to the storage portion, the second mounting position also defining a storage and/or transfer position of the device. In a further aspect of its own, the engagement element is configured to selectively and removably engage the collecting element to the operating portion, so that the collecting element is selectively portable in correspondence with the housing seat and of the storage portion in the first closing position and/or so that the collection portion is selectively portable in correspondence with the housing seat and/or in contact with the storage portion in the first closing position. In a further aspect of its own, the concepts herein also concern the use of a kit in accordance with any of the above-mentioned claims and/or aspects, for collecting, transferring. and storing a sample of a biological and/or chemical material or for collecting, transferring, and storing a sample of a buccal and/or lingual biological material. In a further aspect, the concepts herein concern a method for collecting, transferring and/or storing samples of a biological and/or chemical material by way of a device for collecting, transferring, and/or storing samples of a biological and/or chemical material in accordance with the above mentioned attached claims and/or attached aspects. In a further aspect, combinable with any of the attached claims and/or with any of the further specified aspects, the concepts herein also concern a method for collecting, transferring, and/or storing samples of a biological and/or chemical material comprising at least the step of removing, from the first end of the support body of the device, a separate or pre-indented sub-portion of the first coating layer and of the second coating layer, provided with at least one sample of a biological and/or chemical material. In one aspect, such removal step is performed by way of an appropriate removal tool, such as tweezers, a lancet, a blade tool, or the like. In one aspect, the method also comprises the step of submitting such separate or pre-indented sub-portion to an analysis or storage separate from the remaining sub-portions of the collection portion attached to the first end of the support body. In a further aspect, the concepts herein concern a method for collecting, transferring, and/or storing samples of a biological and/or chemical material by a kit for collecting, transferring, and/or storing samples of a biological and/or chemical material in accordance with the above-mentioned attached claims and/or attached aspects.

The method comprises at least the steps of: collecting a sample of a biological material on at least one collection portion of the collection device, then selectively coupling the collection device with a housing body or with a movable operating portion of the kit, then putting the collection portion of the collecting element in contact with the storage portion of the storage element for samples of a biological material housed in the housing seat of the housing body, to transfer a quantity of the biological material from the collection portion to the storage portion of the storage element. In a further aspect, the method also comprises the step of moving the collection portion of the collecting element away from the storage portion of the storage element and moving the device for collecting and transferring samples of a biological material to a storage and/or transfer position. In a further aspect, the method also comprises the step of storing a sample of a biological material in the storage portion of the storage element for an extended period of time and/or with the device configured in a storage or transfer position. Further aspects of the method for implementing a device for collecting, transferring, and storing samples of a biological and/or chemical material, which might be taken in any combinations between them and/or with the attached claims, are expressed below. In a further aspect of the method the support body is realized by way of an injection molding or extrusion step. In a further aspect, the method comprises the step of gluing the first coating layer to the first end. In a further aspect of the method the step of flocking the second coating layer onto the first coating layer is performed after applying the first coating layer to the first end of the support body. In a further aspect of the method the step of flocking the second coating layer onto the first coating layer is performed before applying the first coating layer to the first end of the support body. In a further aspect of the method the step of flocking the second coating layer onto the first coating layer is performed on a sheet of the first coating layer and wherein the sheet is subsequently cut into portions having appropriate dimensions and subsequently applied to the first end of the support body. In a further aspect of the method the fibers are arranged on the first coating layer by way of a flocking process in an electrostatic field. In a further aspect of the method the fibers are arranged on the first coating layer substantially perpendicular to the surface of the first coating layer. In a further aspect of the method the fibers are arranged on the first coating layer only in correspondence with a front surface of the first coating layer. In a further aspect of the method the fibers are also arranged on the first coating layer in correspondence with a lateral surface of the first coating layer, perpendicular to the front surface.

In a further aspect, the method also comprises the step of indenting or dinking the first coating layer to define a plurality of sub-portions of the first coating layer. In a further aspect of the method the indenting or dinking step is performed so as to realize indentations developing in a direction perpendicular to the surface of the first coating layer intended for receiving the second coating layer. In a further aspect of the method the indentation or dinking step is performed before applying the first coating layer to the first end of the support body. In a further aspect of the method the indentation or dinking step is performed after applying the first coating layer to the first end of the support body. In a further aspect of the method the indenting or dinking step is performed by cutting the first coating layer down to a depth less than the overall thickness of the first coating layer, so as not to completely separate the sub-portions of the first support layer. In a further aspect of the method the indentation or dinking step is performed by cutting the first coating layer all along the depth of the overall thickness of the first coating layer, so as to completely separate the sub-portions of the first support layer. In a further aspect of the method the indentation or dinking step is performed before applying the second coating layer onto the first coating layer. In a further aspect of the method the indenting or dinking step is performed after applying a second layer of adhesive material, suitable for fostering the adhesion of the second coating layer onto the first coating layer, on the first coating layer and before implementing the second coating layer onto the first coating layer. In a further aspect of the method the indenting or dinking step is performed before applying a second layer of adhesive material, suitable for fostering the adhesion of the second coating layer onto the first coating layer, on the first coating layer and before implementing the second coating layer on the first coating layer. In a further aspect of the method the indenting or dinking step is performed after applying the second coating layer on the first coating layer. A detailed description of one or several preferred embodiments is now provided, for explanatory, not limitative purposes, wherein:

FIG. 1 is a perspective view of a device for collecting, transferring, and storing samples of a biological and/or chemical material in accordance with an embodiment of the concepts herein;

FIG. 2 is a front view of the device of FIG. 1;

FIG. 3 shows a side view of the device of FIG. 1;

Figure 4:
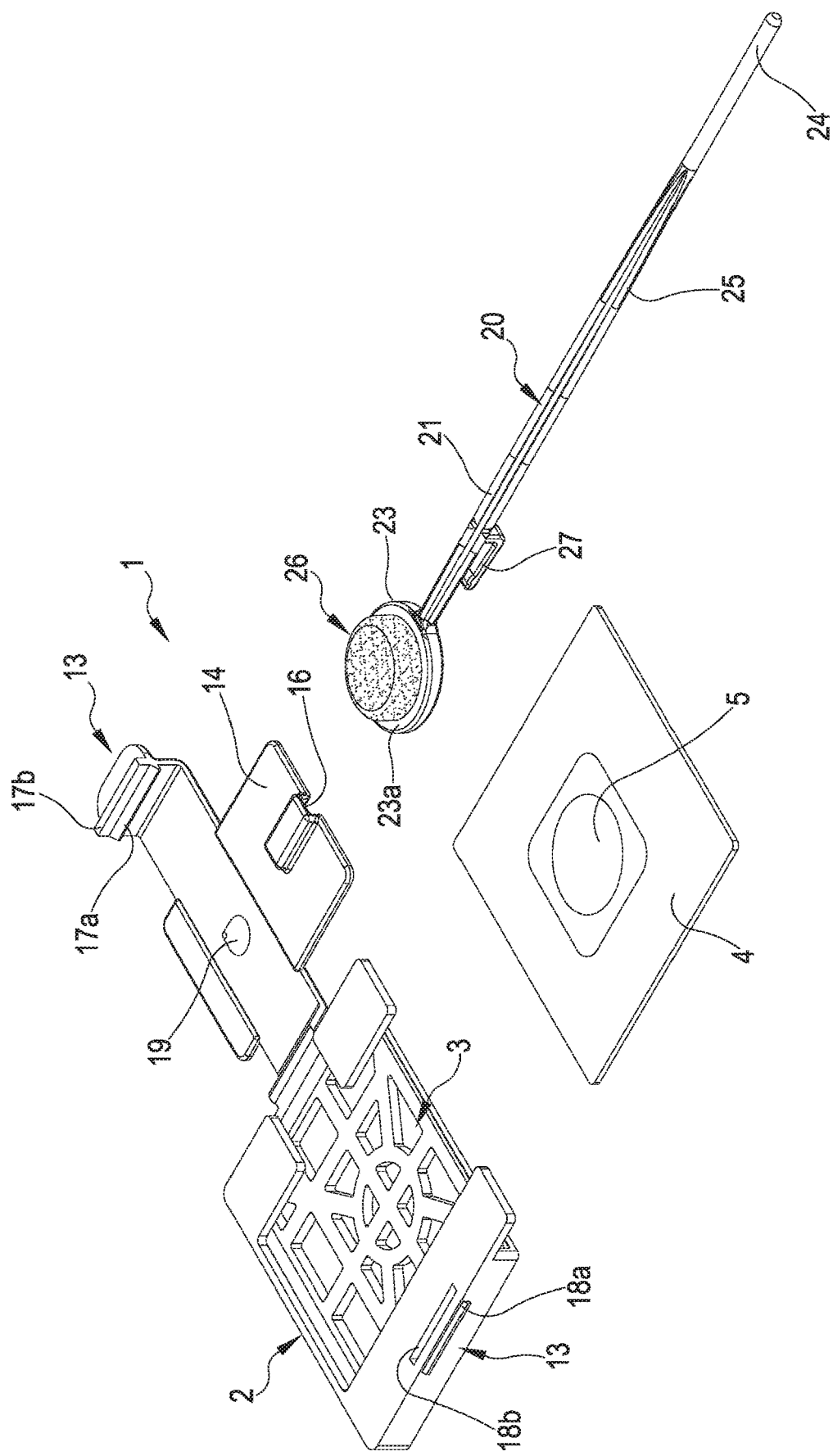
FIG. 4 shows a kit for collecting, transferring, and storing samples of a biological and/or chemical material in accordance with an embodiment of the concepts herein, in a disassembled and opened position, the collection device of FIG. 1 not being coupled with an engagement element of an operating portion of a housing body.
Figure 5:
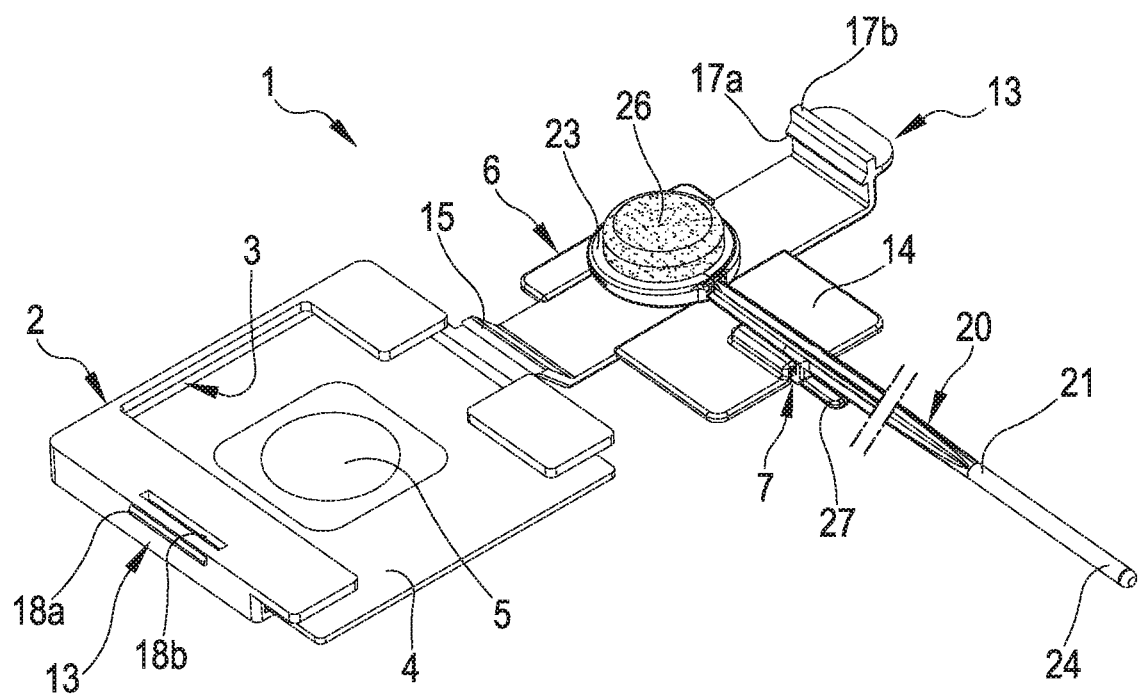
FIG. 5 shows the kit of FIG. 4, the collection device being coupled with an engagement element of the operating portion.
Figure 6:
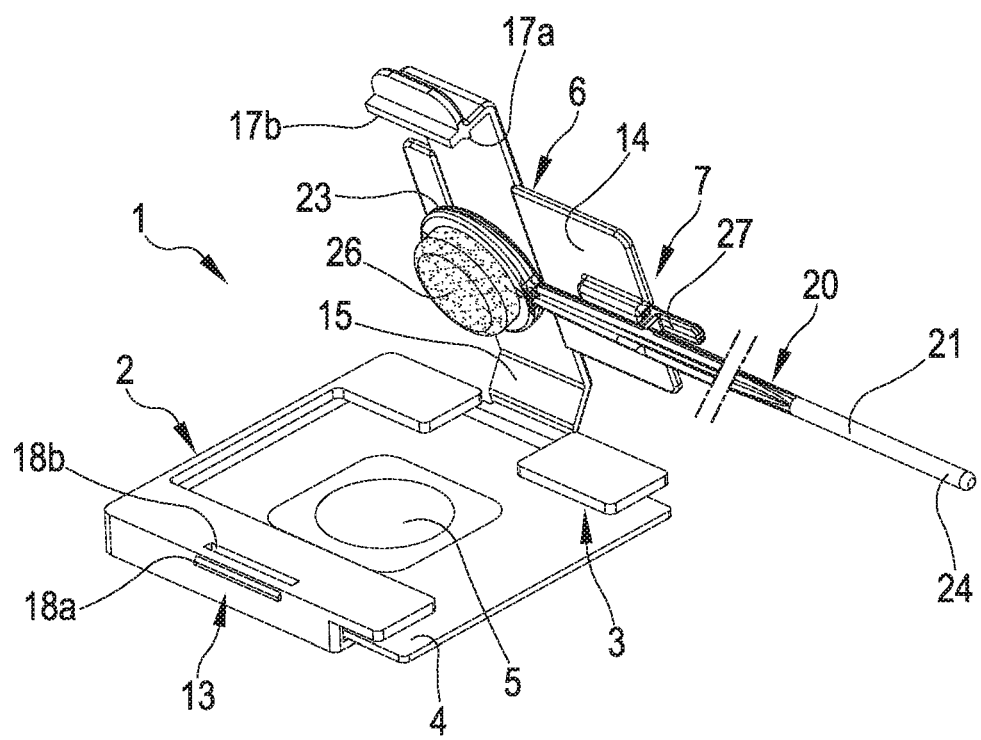
FIG. 6 shows the kit of FIG. 5 in a position intermediate between the opening position and a closing position.
Figure 7:
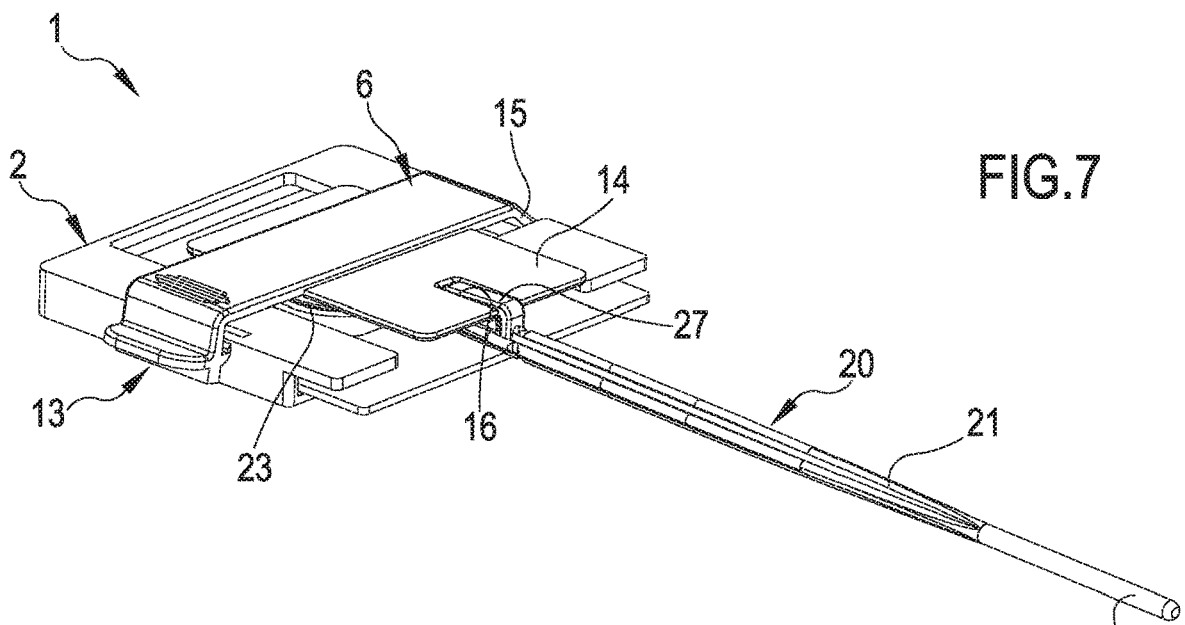
FIG. 7 shows the kit of FIG. 5 in a closing position.

With reference to the figures, the numeral 20 identifies a device for collecting, transferring, and storing samples of a biological and/or chemical material as a whole. In this context, by "biological material" we also mean a microbiological material. Also, by "biological and/or chemical material" we also mean in fact any types of analyte, such as, indicatively but not exhaustively, microorganisms, antibodies/antigens, substances developing an antimicrobic action, nucleotides, antibiotics, hormones, sequences of DNA, enzymes, organic materials, biological materials or materials of biologic origin, enrichment supplements or selective supplements for culture media, and the like, as well as any types of chemical substances. Consequently, such definition comprises samples of different natures intended for a subsequent analysis in the clinical, chemical, biological, microbiological, environmental, genetic, forensic fields and the like. Also, in this text the terms "deformable material" and "elastically deformable material", which a first coating layer of a collection portion of the device 20 is made from, shall be construed as a material that is capable of deforming to an appreciable extent following a stress manually applied by a user to the collection device 20 to make the collection portion of the collection device 20 and here to a storage medium, such as a storage paper, or another medium used to store samples of a biological and/or chemical material commonly used in this sector. The storage paper can be made from cellulose, or from another material suitable for this purpose. More specifically, the "elastically deformable material" which the first coating layer is made from shall be capable of deforming upon getting in contact with such storage medium to increment the adhesion and the surface of exchange between the collection portion, and in particular of the first and second coating layer, and the support surface of the storage medium put in contact with such layers. Also, by this term "elastically deformable material" we mean a material having a greater deformability with respect to the material that the support body 21 of the collection device 20 and its first end are made from. Finally let's point out that in this context the wording "device for collecting, transferring, and storing samples of a biological and/or chemical material" does not include those devices, typically disposable but even re-usable after washing, which are solely configured and intended for cleaning portions of a user's mouth, and not specifically to collect samples for analytical purposes, for instance for laboratory, forensic and/or medical applications, consequently this definition does not include, for instance, toothpicks and devices for tongue, tooth, and gum cleaning. The device 20 for collecting, transferring, and storing samples of a biological and/or chemical material comprises at least one support body 21, developing along a main longitudinal direction 22 from a first end 23 to a second end 24 opposite to each other and interconnected by an intermediate portion 25 featuring an elongate shape in the main longitudinal direction 22. The support body 21 is preferably made from a substantially rigid or partially flexible material and, for instance, from a plastic material. The support body 21 might be for instance made from a plastic polymer or co-polyester or polystyrene or nylon/polyamide or another material suitable for this purpose. The device 20 also comprise at least one collection portion 26 engaging the first end 23 and configured to collect a quantity of a sample of a biological and/or chemical material. The collection portion 26 is configured to collect or absorb a quantity ranging from 5 to 1000 microliters of a sample. Preferably this quantity ranges from 10 microliters to 500 microliters, and even more preferably from 50 to 250 microliters of a sample. The collection portion 26 is defined at least by one first coating layer 26a made from an elastically deformable material realized on the first end 23 and by at least one second coating layer 26b consisting of a layer of flocked fibers, the second coating layer 26b being realized through a fiber flocking process on the first coating layer 26a and being configured to absorb a quantity of liquid comprising at least one sample of a biological and/or chemical material. The collection portion 26 is configured to collect or absorb a substantially known quantity of a sample, and in particular the fibers are arranged on the first coating layer 26a so as to define a plurality of capillary interstices suitable for absorbing the sample by capillarity. Preferably is a first layer of adhesive material arranged between the first coating layer 26a and the first end 23 to attach the first coating layer 26a at least to the front face of the first end 23. Alternatively, a step might be provided of heating the material of the first end 23 and/or of the first coating layer 26a so as to make such materials capable of stably adhering to each other even after their cooling down. Preferably is a second layer of adhesive material provided between the first coating layer 26a and the second coating layer 26b, to make it possible for the flocked fibers to adhere to the first coating layer 26a, during the flocking process.

The adhesive material might be, for instance, a vinylic adhesive or an adhesive of another type suitable for this purpose. In this case too, as an alternative, there might be provided a step of heating the material of the first coating layer 26a so as to make such material suitable for determining the adhesion of the fibers in a stable manner even after their cool down. The second coating layer 26b formed of a flocking layer can be realized for instance according to the teachings of the already mentioned patent EP1608268B1 or patent applications WO2014/049460 and WO2014/207598, on behalf of this Applicant, and whose content concerning the type of the fibers used and the arrangement and characteristics of the layer of flocking fibers is incorporated in the present text for reference. Specifically, the fibers are arranged by the flocking process on the first coating layer 26a in a substantially orderly manner. Preferably are the fibers arranged on the first coating layer 26a so as to form a substantially continuous layer. The fibers preferably feature a count ranging from 1 to 10 dtex, or from 2 to 7 dtex, or from 3 to 5 dtex. The fibers preferably feature a length ranging from 0.2 mm to 3 mm, or from 0.4 mm to 2 mm, or from 0.6 mm to 1.5 mm. The fibers can be made, for instance, from a polyamide (PA or nylon) and/or rayon and/or polyester and/or carbon fiber and/or alginate and/or natural fiber and/or cotton and/or a mix of such materials. The collection portion 26 can feature, for instance, a surface density of fibers on the first coating layer 26a ranging from 50 to 1,000 fibers per $mm^2$ or from 100 to 500 fibers per $mm^2$. The first end 23 preferably features a shape, transversally to the main longitudinal direction 22 widened, with respect to the intermediate portion 25, and is provided at least with one front face 23a and one rear face 23b, reciprocally facing each other. Preferably the front face 23a and/or the flocked portion and/or the rear face 23b feature a substantially flat configuration. Alternatively, the front face 23a and/or the flocked portion and/or the rear face 23b might feature a configuration defined by a curved surface. Preferably is such curve convex. The front face 23a and the rear face 23b can be substantially equal to each other and/or symmetrical. The thickness of the first end 23, as measured between the first face and the second face and/or in a direction perpendicular to the first face and/or to the second face, can range from 0.5 mm to 5 mm, or from 0.7 to 4 mm, or from 1 to 2.5 mm. The surface of the front face 23a and/or of the rear face 23b can range from 20 $mm^2$ to 1250 $mm^2$, or from 80 $mm^2$ to 700 $mm^2$, or from 120 $mm^2$ to 400 $mm^2$. The width 30 of the front face 23a and/or of the rear face 23b, in a direction perpendicular to the main longitudinal direction 22, can range from 5 mm to 40 mm, or from 10 mm to 30 mm, or from 12 mm to 22 mm. Such length coincides with the diameter of such faces, should the latter feature a circular shape, as illustrated. The collection portion 26 can have a length 31 ranging from 5 mm to 40 mm, or from 10 mm to 30 mm, or from 15 mm to 25 mm, or from 12 mm to 20 mm. The collection portion 26 is engaged at least to the front face 23a of the first end 23 and the first coating layer 26a and the second coating layer 26b are present at least on a portion of the front face 23a of the first end 23. In the preferred embodiment, the collection portion 26 is uniquely defined on the front face 23a of the first end 23 and is absent on the rear face 23b, as illustrated in the attached figures. In a variant not shown here, the collection portion 26 can also be defined on the rear face 23b of the first end 23. In one embodiment, the first layer 26a is made from a liquid-impermeable and/or hydrophobic material. In one embodiment, the first layer 26a is liquid-impermeable. In one alternative embodiment, the first coating layer 26a can be made from a liquid-absorbing and/or spongy material. In particular, the first layer 26a can be a liquid-absorbing one and have an additional absorbing capability with respect to an absorbing capability of the second coating layer 26b. The first coating layer 26a can, for instance, be made from an elastomeric material. The absorbing capability of the collection portion 26 can be fully defined by the second layer coating layer 26b alone, for instance in the case the first coating layer 26a is liquid-impermeable. The second coating layer 26b can be configured to collect or absorb a quantity ranging from 5 to 1000 microliters, or from 10 microliters to 500 microliters, or from 50 to 250 microliters of a sample. In a preferred embodiment, as illustrated in the figures, the first coating layer 26a covers the first end 23 only partially, and in particular it covers the front face 23a only of the first end 23. Alternatively, the first coating layer 26a can fully cover the front face 23a of the first end 23, or in other alternatives it can fully covers the rear face 23b too or the complete first end 23. In the embodiment here illustrated, the second coating layer 26b fully covers the first coating layer 26a, both in correspondence with one front face 23a thereof, and in correspondence with a lateral surface perpendicular to the front face 23a.

Figure 8:
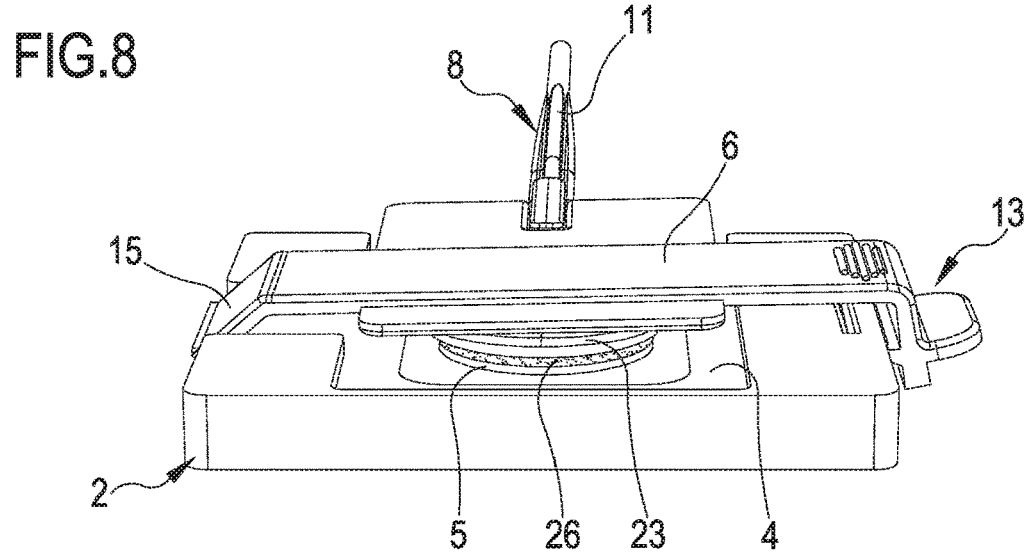
FIG. 8 shows a detail of the kit of FIG. 5 in a first closing and/or sample contact and transfer position.
Figure 9:
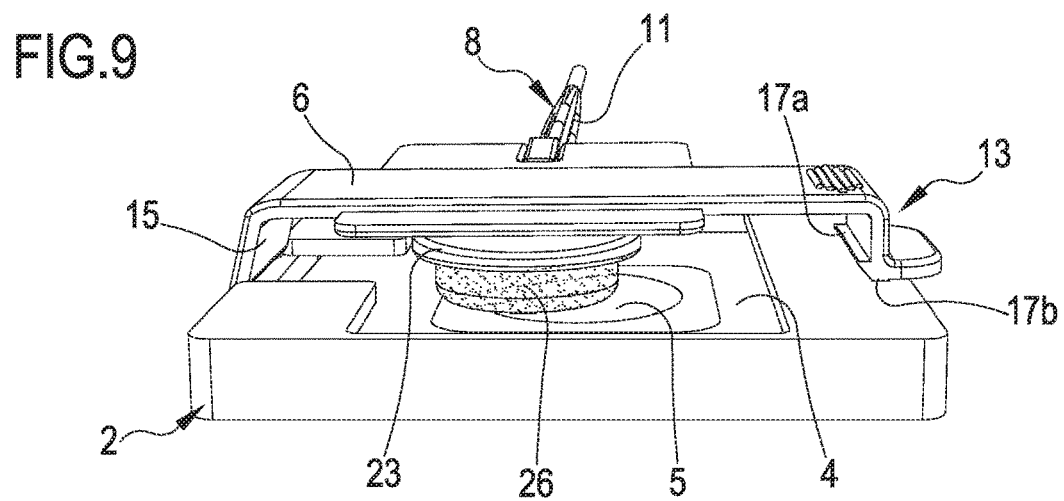
FIG. 9 shows a detail of the kit of FIG. 5 in a second closing and/or storage and transfer position of the kit.

In a variant, not illustrated here, the second coating layer 26b can cover the first coating layer 26a only partially. In the variant wherein the first coating layer 26a is also present on the rear face 23b of the first end 23, the first coating layer 26a can cover the rear face of the first end 23 only partially. The thickness 32 of the first coating layer 26a is preferably less than 6 mm, or less than 5 mm, or less than 4 mm, or less than 3 mm. The thickness 32 of the first coating layer 26a is preferably greater than 0.5 mm, or greater than 1 mm, or greater than 2 mm. The thickness 33 of the second coating layer 26b is preferably less than 3 mm, or less than 2 mm, or less than 1.5 mm. The thickness 33 of the second coating layer 26b is preferably less than 0.2 mm, or greater than 0.4 mm, or greater than 0.6 mm. In an alternative embodiment, not illustrated here, the first coating layer 26a can be formed of a plurality of separate sub-portions and/or be provided with a plurality of pre-indented sub-portions. For instance, the first coating layer 26a can be provided with indentations cut in such a way as to define a plurality of at least partially separate sub-portions, so as to make the detachment of at least one single sub-portion of the first coating layer 26a, and of the corresponding sub-portion of the second layer 26b, from the first end 23 easier at a time following sample collection. The support body 21 is preferably provided, for instance in correspondence with the intermediate portion 25, with a coupling portion 27. In particular, the collection device 20 can be a buccal collecting swab or a buccal or lingual one. In the present text, by "buccal" we mean a collection of a biological sample that is made in a patient's mouth, and consequently also comprises a lingual collection or the like. In any case, the concepts herein might find applications, in one or more of its aspects, for collections of types different from buccal collection, for instance for collections in other cavities of the body or for collections blood samples. A detailed description of a preferred explanatory embodiment of a kit for collecting, transferring, and/or storing samples of a biological material, identified by the reference numeral 1 as a whole, is provided below. This kit comprises at least one housing body 2 having at least one housing seat 3 for a storage element 4 for samples of a biological material. The housing seat 3 is configured to make it possible to removably house the storage element 4 for samples of a biological material. The storage element 4 is preferably a chemically treated paper suitable for storing samples of a biological material, and in particular a paper comprising at least one substance capable of storing a sample of a biological material, in particular suitable for storing a buccal sample. Alternatively, the element 4 might be a different medium type suitable for this purpose. The housing seat 3 can consequently be configured to make it possible to removably house such chemically treated paper for storing biological samples, and preferably it is configured as a lateral opening of the housing body 2 into which the paper can be slidingly inserted. The housing body 2 is configured to have at least one storage portion 5 of the storage element accessible for depositing a sample of a biological material whenever the storage element is housed in the housing seat 3, for instance by way of a front opening, with respect to the mentioned lateral opening. The kit 1 also comprises an operating portion 6 movable at least between a first closing position wherein it is arranged close to the housing seat 3 and at least one opening position wherein it is arranged in a position spaced away from the housing seat 3. The kit 1 also comprises an engagement element 7 configured to selectively and removably engage a collection device 20 of the above illustrated type to the kit 1, and in particular to the housing body 2 and/or to the operating portion 6. The device 20 is selectively and removably couplable with the engagement element 7 by way of the coupling portion 27. Further characteristics of the collecting kit and further variants, equally applicable in combinations with the concepts herein, are illustrated in the already mentioned patent application WO2014/001940 (Triva), whose contents, as far as possible specific embodiments of kit are concerned, is incorporated in the present description for reference. In the embodiments illustrated in the present patent application, the engagement element 7 is configured to selectively and removably engage the collection device 20 for samples of a biological material to the operating portion 6, so that the collection device 20 is selectively portable, as a consequence of the operating portions 6 being moved, in correspondence with the housing seat 3 and of the storage portion 5 in the first closing position and/or so that the collection portion 26 is selectively portable in correspondence with the housing seat 3 and/or in contact with the storage portion 5 in the first closing position. The kit can also comprise a closure 13 suitable for selectively closing the kit 1 at least in the first closing position, shown in detail in FIG. 8, wherein a contact and a transfer of a biological material take place from the collection portion 26 to the storage portion 5. The closure 13 is preferably suitable for also defining at least one second closing position, illustrated in details in FIG. 9, wherein the collection portion 26 is spaced away from the storage portion 5 and consequently there is no contact nor transfer of a biological material between the two mentioned portions, the second closing position also advantageously defining a storage and/or transfer position of the kit 1. The operating portion 6 can comprise a closing element or cover 14 suitable for at least partially covering, at least in the first closing position and/or in the second closing position, the housing seat 3 and/or for at least partially covering and protecting the storage element 4 for samples of a biological material housed in the housing seat 3 and/or for covering and protecting the storage portion 5 for samples of a biological material during the storage and/or transfer of the kit and/or at least in the second closing position and/or at least in the second mounting position. The operating portion 6 can be engaged in a non-removable manner to the housing body 2, for instance it can be made as one-piece with the housing body 2. In one variant, the operating portion 6 can be removably engaged to the housing body 2. In the embodiments illustrated in the attached figures, the operating portion 6 is joined to the housing body 2 by an elastically deformable connection portion 15. In one variant, the connection portion 15 can be plastically deformable. At least the housing body 2, the operating portion 6, the engagement element 7, the connection portion 15, the collection device 20 and/or the coupling portion 27 are preferably made from a plastic material. For instance, the housing body 2, the operating portion 6, the engagement element 7, and the connection portion 15 can be made from polypropylene, whereas the collection device 20 and/or the coupling portion 27 can be made for instance from polystyrene. The engagement element 7 can comprise for instance a coupling seat 16 wherein the coupling portion 27 of the collection device 20 is selectively, slidingly and/or snap-in, and/or rotationally inserted, or in another manner suitable for this purpose. In one variant, the coupling portion 27 can be inserted into a coupling seat 16 defining a sliding guide suitable for allowing for a translation of the collection device 20 with respect to the housing body 2 and/or in correspondence with the storage element 4. Vice versa, alternatively, a coupling seat might be provided on the collection device and a coupling portion might be provided on the engagement element 7. The closure 13 can comprise at least one attachment portion 17 realized on the operating portion 6 and at least one attachment seat 18 realized on the housing body 2. Vice versa, alternatively, an attachment seat might be provided on the operating portion 6 and an attachment portion might be provided on the housing body 2. The closure 13 can comprise at least two separate attachment portions 17a, 17b selectively engageable in the attachment seat 18, to define the first and second closing positions respectively. The closure 13 can comprise at least two separate attachment seats 18a, 18b with the attachment portion 17 to define the first and second closing positions respectively. In the embodiment here illustrated, the attachment portion 17 comprises at least two separate attachment zones 17a, 17b, suitable for engaging each a respective separate attachment seat 18a, 18b to define the first and second closing positions respectively (illustrated in FIGS. 8 and 9 respectively). The kit 1 can also comprise a bulging element 19 of the movable element 6 suitable for acting onto the collection portion 26 to force it in contact with the storage portion 5 and make it possible an optimum and as much uniform as possible transfer of a biological material.

The concepts herein also concern a method to implement a device 20 for collecting, transferring, and storing samples of a biological and/or chemical material of the above described type. The method comprises at least the following steps: realizing the support body 21 including at least the first end 23, the second end 24, and the intermediate portion 25; realizing the collection portion 26 on the first end 23 of the support body 21, by realizing and securing the first coating layer 26a to the first end 23 and by realizing the second coating layer 26b by flocking a layer of fibers onto the first coating layer 26a. The support body 21 can be for instance realized by injection molding or extrusion. The method can also comprise a step of gluing the first coating layer 26a to the first end 23. The step of flocking the second coating layer 26b onto the first coating layer 26a can be performed either before or after applying the first coating layer 26a to the first end 23 of the support body 21. For instance, the step of flocking the second coating layer 26b onto the first coating layer 26a can be performed on a sheet of the first coating layer 26a and the sheet can subsequently be cut into portions of appropriate dimensions and subsequently applied to the first end 23 of the support body 21. Preferably are the fibers arranged on the first coating layer 26a by a flocking process in an electrostatic field, preferably in a substantially perpendicular manner to the surface of the first coating layer 26a. The fibers can be arranged on the first coating layer 26a exclusively in correspondence with the front surface of the first coating layer 26a, or even in correspondence with a lateral surface of the first coating layer 26a, perpendicular to the front surface, as illustrated in the figures. In one variant, the method can also comprise a step of indenting or dinking the first coating layer 26a to define a plurality of sub-portions of the first coating layer 26a. Such step of indenting or dinking is preferably performed so as to realize indentations developing in a direction perpendicular to the surface of the first coating layer 26a intended for receiving the second coating layer 26b. The indenting or dinking step can be performed either before or after applying the first coating layer 26a to the first end 23 of the support body 21. Such step can for instance be performed by cutting the first coating layer 26a down to a depth less than the overall thickness of the first coating layer 26a, so as not to completely separate the sub-portions of the first support layer 26a, or alternatively it can be performed by cutting the first coating layer 26a all along the depth of the overall thickness of the first coating layer 26a, so as to completely separate the sub-portions of the first coating layer 26a. The indenting or dinking step can be performed before applying the second coating layer 26b onto the first coating layer 26a. This step can be performed after applying a second layer 26b of adhesive material, suitable for allowing for the adhesion of the second coating layer 26b onto the first coating layer 26a, onto the first coating layer 26a and before realizing the second coating layer 26b on the first coating layer 26a. Such step can be performed before applying a second layer 26b of adhesive material, suitable for allowing for the adhesion of the second coating layer 26b onto the first coating layer 26a, onto the first coating layer 26a and before realizing the second coating layer 26b onto the first coating layer 26a. Alternatively such step can be performed after applying the second coating layer 26b onto the first coating layer 26a. The concepts herein also concern a method for collecting, transferring, and/or storing samples of a biological material by a device 20 and/or a kit 1 of the above-mentioned type. The method can comprise for instance at least the following steps: collecting a sample of a biological material onto at least one collection portion 26 of a collecting element 20, preferably a buccal sample. If the first coating layer 26a is impermeable, the quantity of the sample is fully absorbed by the second flocked coating layer 26b, whereas in the case the first coating layer 26a is also absorbing, then an additional quantity of liquid comprising the sample can be collected therein. The method also comprises the step of subsequently and selectively coupling the collection device 20 with a housing body 2 or with a movable operating portion 6 of the kit 1, then bringing the collection portion 26 of the collection device 20 in contact with a storage portion 5 of a storage element 4 for samples of a biological material housed in a housing seat 3 of the housing body 2 to transfer a quantity of the biological material from the collection portion 26 of the collection device 20 to the storage portion 5. Thanks to the presence of the first deformable coating layer 26a, an optimum compression is made of the second flocked coating layer 26b and consequently is possible to optimize the transfer of the collected quantity of sample, even in the case the first layer 26a is impermeable and/or the sample has not been absorbed. If the first layer 26a is also an absorbing one, and consequently it absorbed an additional quantity of liquid comprising the sample, a part of such additional quantity can also be released towards the storage portion 5 thanks to the pressure exerted during transfer. This method can also comprise a step of subsequently moving the collection portion 26 away from the storage portion 5 of the storage element 4 to bring the kit 1 to a storage and/or transfer position. The method can also comprise a step of storing the sample of a biological material on the storage portion 5 for a period of time, the kit 1 being preferably configured in a storage or transfer position. The method can also comprise a step of removing one or more of the separate and/or pre-indented sub-portions from the collection portion 26, for a separate use of a part of the collected sample. The concepts herein also concern the use of a device 20 and/or a kit 1 of the above-mentioned type, for collecting, transferring, and/or storing a sample of a biological material and/or for a buccal collection, transfer, and storage of a sample of a buccal biological material. The concepts herein make it possible to achieve at least one or more of the following advantages. First of all, the concepts herein make it possible to solve one or more of the problems encountered in the known art. The concepts herein also guarantee a reliable and fully traceable storage of the collected sample. The concepts herein also provide a high reliability in any operating conditions and as much independently as possible of the modes of use by a specific professional user. The concepts herein also allow for an optimum transfer of a sample collected from a collection device to a storage paper or to another storage or analysis medium. The concepts herein are also easy to use. The concepts herein also allow to reduce the risk of contaminating the collected samples. Finally, the concepts herein are simple and economical to implement.

The invention claimed is:

1. A device for collecting, transferring, and storing samples of a biological and/or chemical material, wherein the device comprises:
    a support body, developing along a main longitudinal direction between a first end and a second end opposite to each other and connected by an intermediate portion elongate in the main longitudinal direction,
    a collection portion engaging the first end and configured to collect a quantity of a sample of a biological and/or chemical material, the collection portion being defined at least by one first coating layer realized on the first end and made from a deformable material, preferably an elastically deformable material, and by one second coating layer comprising a layer of flocked fibers, the second coating layer being realized through a fiber flocking process onto the first coating layer and being configured to absorb a quantity of liquid including at least one sample of a biological and/or chemical material, wherein the first coating layer is liquid-impermeable and wherein the first coating layer comprises a plurality of separate sub-portions and/or is provided with a plurality of pre-indented sub-portions and/or is provided with indentations realized in such a way as to define a plurality of at least partially separate sub-portions, so as to facilitate the detachment of at least one individual sub-portion of the first coating layer, and of a corresponding sub-portion of the second layer, from the first end at a time following sample collection.

2. A device according to claim 1, wherein the first end has a widened shape transversally to the main longitudinal direction with respect to the intermediate portion, and is provided at least with one front face and one rear face opposed to each other, the collection portion engaging at least the front face of the first end and the first coating layer and the second coating layer being present at least on one part of the front face of the first end.

3. A device according to claim 2, wherein the front face and/or the layer of flocked fibers and/or the rear face feature a substantially flat shape.

4. A device according to claim 2, wherein the front face and/or the layer of flocked fibers and/or the rear face feature a shape defined by a curved surface or by a curved and convex surface.

5. A device according to claim 2, wherein the first coating layer covers the front face of the first end only partially, and/or wherein the first coating layer covers the rear face of the first end only partially, and/or wherein the first coating layer covers the first end only partially, and/or wherein the second coating layer covers the first coating layer only partially.

6. A device according to claim 1, wherein the first end has a widened shape transversally to the main longitudinal direction with respect to the intermediate portion and is provided at least with one front face and one rear face, opposed to each other, wherein the collection portion is exclusively defined on the front face of the first end and is not present on the rear face.

7. A device according to claim 1, wherein the collection portion is configured to collect or absorb a quantity ranging from 5 to 1000 microliters, or from 10 microliters to 500 microliters, or from 50 to 250 microliters of a sample, or wherein the second coating layer is configured to collect or absorb a quantity ranging from 5 to 1000 microliters, or from 10 microliters to 500 microliters, or from 50 to 250 microliters of a sample.

8. A device according to claim 1, wherein the first coating layer has a thickness which is less than 6 mm, or less than 5 mm, or less than 4 mm, or less than 3 mm and/or greater than 0.5 mm, or greater than 1 mm, or greater than 2 mm.

9. A device according to claim 1, wherein the second coating layer has a thickness which is less than 3 mm, or less than 2 mm, or less than 1 mm and/or greater than 0.3 mm, or greater than 0.45 mm, or greater than 0.6 mm.

10. A device according to claim 1, wherein the first coating layer is made from a liquid-impermeable and/or hydrophobic material and/or wherein the first coating layer is made from an elastomeric material.

11. A device according to claim 1, wherein the first coating layer is made from one or more of the following materials: synthetic sponge, expanded resin, expanded polyethylene, EVA, LDPE, expanded polyurethane, polyether, polyester, Stratocell®, Antistatic, foam, Plastazote®, rubber mousse, latex, Dryfeel®.

12. A device for collecting, transferring, and storing samples of a biological and/or chemical material, wherein the device comprises:
    a support body, developing along a main longitudinal direction between a first end and a second end opposite to each other and connected by an intermediate portion elongate in the main longitudinal direction,
    a collection portion engaging the first end and configured to collect a quantity of a sample of a biological and/or chemical material, the collection portion being defined at least by one first coating layer realized on the first end and made from a deformable material, preferably an elastically deformable material, and by one second coating layer comprising a layer of flocked fibers, the second coating layer being realized through a fiber flocking process onto the first coating layer and being configured to absorb a quantity of liquid including at least one sample of a biological and/or chemical material, wherein the first coating layer comprises a plurality of separate sub-portions.

13. A device according to claim 12, wherein the first end has a widened shape transversally to the main longitudinal direction with respect to the intermediate portion and is provided at least with one front face and one rear face, opposed to each other, wherein the collection portion is exclusively defined on the front face of the first end and is not present on the rear face.

14. A device according to claim 12, wherein the first coating layer is made from a liquid-absorbing material and/or a spongy material and/or wherein the first layer is liquid-absorbing and features an additional absorbing capability with respect to an absorbing capability of the second coating layer and/or wherein the first coating layer is made from an elastomeric material.

15. A device for collecting, transferring, and storing samples of a biological and/or chemical material, wherein the device comprises:

a support body, developing along a main longitudinal direction between a first end and a second end opposite to each other and connected by an intermediate portion elongate in the main longitudinal direction, a collection portion engaging the first end and configured to collect a quantity of a sample of a biological and/or chemical material, the collection portion being defined at least by one first coating layer realized on the first end and made from a deformable material, preferably an elastically deformable material, and by one second coating layer comprising a layer of flocked fibers, the second coating layer being realized through a fiber flocking process onto the first coating layer and being configured to absorb a quantity of liquid including at least one sample of a biological and/or chemical material, wherein the first coating layer is provided with a plurality of pre-indented sub-portions and/or is provided with indentations realized in such a way as to define a plurality of at least partially separate sub-portions, so as to facilitate the detachment of at least one individual sub-portion of the first coating layer, and of a corresponding sub-portion of the second coating layer, from the first end at a time following sample collection.

16. A device according to claim 15, wherein the first end has a widened shape transversally to the main longitudinal direction with respect to the intermediate portion and is provided at least with one front face and one rear face, opposed to each other, wherein the collection portion is exclusively defined on the front face of the first end and is not present on the rear face.

17. A device according to claim 15, wherein the first coating layer is made from a liquid-absorbing material and/or a spongy material and/or wherein the first layer is liquid-absorbing and features an additional absorbing capability with respect to an absorbing capability of the second coating layer and/or wherein the first coating layer is made from an elastomeric material.

* * * * *